United States Patent [19]

Goodnow

[11] 4,152,413

[45] May 1, 1979

[54] ORAL VACCINE FOR SWINE DYSENTERY AND METHOD OF USE

[75] Inventor: Robert A. Goodnow, Omaha, Nebr.

[73] Assignee: Chromalloy American Corporation, Clayton, Mo.

[21] Appl. No.: 934,812

[22] Filed: Aug. 18, 1978

[51] Int. Cl.$^2$ .................. A61K 39/02; A61K 9/28; A61K 9/30; A61K 9/36

[52] U.S. Cl. .................................. 424/16; 424/35; 424/92

[58] Field of Search ............. 424/16, 31, 35, 88, 424/89, 92, 93

[56] References Cited

U.S. PATENT DOCUMENTS

| | | | |
|---|---|---|---|
| 2,369,218 | 2/1945 | Dick et al. | 424/92 X |
| 2,946,724 | 7/1960 | Valentine | 424/89 |
| 3,072,528 | 1/1963 | Kludas et al. | 424/93 |
| 3,081,233 | 3/1963 | Enz et al. | 424/35 X |
| 3,127,318 | 3/1964 | Eversole et al. | 424/92 X |
| 3,317,393 | 5/1967 | Chanock et al. | 424/89 X |
| 3,458,621 | 7/1969 | Tint | 424/35 X |
| 3,541,203 | 11/1970 | Fogle et al. | 424/93 X |
| 3,823,228 | 7/1974 | Ferris et al. | 424/35 |

OTHER PUBLICATIONS

Hudson M. J. et al., Res. Vet. Sci. 1976 21(3): 366–367, Swine Dysentery: Protection of Pigs by Oral and Parenteral Immunization with Attenuated Treponema Hyodysenteriae.

*Primary Examiner*—Shep K. Rose
*Attorney, Agent, or Firm*—Haverstock, Garrett and Roberts

[57] ABSTRACT

An oral preparation for increasing the resistance of swine to swine dysentery infection comprises enteric-coated orally-administrable pellets containing concentrated killed cells of a virulent isolate of *Treponema hyodysenteriae*. In the preferred method of use, the preparation is orally administered to swine in a plurality of doses providing at least 3 mg. of the cells per animal per dose.

12 Claims, No Drawings

ORAL VACCINE FOR SWINE DYSENTERY AND METHOD OF USE

An anaerobic spirochete, *Treponema hyodysenteriae*, has been characterized as the primary etiological agent in swine dysentery. Harris, D. L.; Glock, R. D.; Christensen, C. R.; and Kinyon, J. M.: *Vet. Med./Small Animal Clin.* 67:61 (1972); Taylor, D. J.; and Alexander T. J. L.: *Brit. Vet. J.* 127:108 (1971). But relatively little is known about the immunology of swine dysentery although resistance to reinfection can be demonstrated in convalescent pigs. In 1976, Glock et al reported that parenteral vaccination of pigs with killed cells of a virulent isolate of *T. hyodysenteriae* provided a significant degree of protection against subsequent intragastric challenge with live virulent *T. hyodysenteriae*. Glock, R. D., Schwartz, K. J., and Harris, D. L., *Proceedings, International Pig Veterinary Society Congress*, June 1976, Ames, Iowa. The vaccine was given in six intravenous injections at 6-day intervals. This was the first reported success in immunizing swine against swine dysentery infection. For field use, an oral vaccine would be more convenient to use. However, previous attempts to develop an oral vaccine have produced discouraging results.

Hudson et al found that oral dosing of an attenuated strain of *T. hyodysenteriae* provided no protection against subsequent challenge. Hudson, M. J., Alexander, T. J. L., Lysons, R. J., Wellstead, P. D., *Brit. Vet. J.* (1974) 130:37. Subsequently, Hudson et al attempted to immunize pigs with live attenuated *T. hyodysenteriae* using a combination of oral dosing and parenteral inoculation. Hudson, M. J., Alexander, T. J. L., Lysons, R. J., Prescott, J. F., *Res. Vet. Science* (1976) 21:366. Oral doses were administered on three consecutive days, and after an interval of several days, intraperitoneal vaccinations were administered, which were followed after several more days by intramuscular vaccinations. The overall results of these tests were summarized as follows: "Although vaccination appeared to enhance immunity to swine dysentery, half of the vaccinated pigs developed the disease. This level of protection would be unlikely to be of practical value in the field."

SUMMARY OF INVENTION

The present invention is based in part on the discovery that the resistance of swine to dysentery infection can be increased by orally administering enteric-coated pellets containing concentrated killed cells of a virulent isolate of *Treponema hyodysenteriae*. The enteric coating is selected so that it will be resistant to dissolving in the swine stomach while dissolving in the swine intestines to release the killed cells for immunizing action. Preferably, the enteric coating is substantially insoluble in water at a pH below 5.0, while becoming slowly soluble in water at a pH of 5.8 to 6.2. Oral preparations prepared in accordance with the present invention are particularly useful for administration to young pigs which are subject to swine dysentery infection. For this purpose, the oral vaccine is prepared in the form of enteric-coated granules, which are mixed with a finely-divided feed material, and fed to pigs on the basis of a regimen which provides massive introduction of the killed cells into the colon area. Preferably, the immunizing feed is administered to the pigs at least onece every 24 hours for a period of at least five days with each feeding providing at least 3 milligrams of the cells (dry basis) per animal.

Other features and advantages of the invention will be described in the following specification.

DETAILED DESCRIPTION

The present invention can be practiced with any virulent isolate of *T. hyodysenteriae*. Attenuated or nonvirulent isolates or strains are not desirable. A virulent isolate or strain is one which is capable of producing a typical swine dysentery infection. One suitable isolate has heretofore been identified in the literature as B204. See Kinyon, J. M., and Harris, D. L.: *Vet. Rec.* (1974): 95:219. The same publication also refers to an isolate identified as B234, which can also be used in practicing the present invention. However, type strain B78 (ATCC No. 27164) is not suitable, being nonvirulent. Isolates B204 and B234 have been deposited with the American Type Culture Collection; B204 being identified as ATCC No. 31212 and B234 as ATCC No. 31287. It should be understood that these isolates are representative of class of virulent isolates or strains which can be employed.

The *T. hyodysenteriae* cells for preparation of the oral vaccine can be cultured using trypticase soy broth (TSB) with 10% (v/v) fetal calf serum (FCS). For example, the inoculated broth can be incubated at 37°-38° C. under an anaerobic atmosphere, such as 50:50 $H_2$:$CO_2$ or $CO_2$ alone. The gaseous atmosphere should be deoxygenated. For further details, see Kinyon, J. M., and Harris D. L.: *Vet. Rec.* (1974): 95:219.

After the fermentation has been completed, the cells can be recovered and concentrated by centrifugation or ultrafiltration to obtain a cell slurry for further processing. The cells are killed by a suitable procedure either in the fermenter or after recovery. Standard killing agents may be used such as formalin or merthiolate. For example, a killing-concentration of formalin, such as 0.2% formalin (v/v), can be added to the fermenter or cell slurry. The slurry of killed cells is used to prepare the enteric-coated pellets.

To act as a filler or bulk stabilizer for desiccation and pellet preparation, standard filler substances may be added to the cell slurry such as sucrose, dextrose, lactose, etc. In general, the amount of filler-stabilizer to be added may range from about 10 to 50 parts by weight of filler per 100 parts of cells (dry basis). Prior to the addition of the filler, the cell concentrate preferably contains in excess of 3.0 milligrams of cells (dry basis) per millileter of slurry. For example, the cell concentrates may contain from about 4 to 7 milligrams of cells (dry basis) per milliliter of cell slurry. The particular concentration is not critical, since most of the residual water of the slurry is removed by a suitable drying procedure in preparing the pellets.

For example, a 1:10 dilution of sterile 50% non-fat powdered milk plus 50% $H_2O$ solution to act as filler-stabilizer was added to the concentrated slurry (4.0 mg/ml dry weight antigen). This material was dried by a biological drying procedure such as freeze-drying.

The cell slurry containing the added filler may be dried by a biological drying procedure such as freeze-drying. Preferably, the drying is carried out at a relatively low temperature, such as not over 40° C. The dried material is then pulverized to a finely-divded condition for preparing tablets or granules. If desired, a binder material such as starch may be added at this point, although the filler may provide adequate binding.

Tablets may then be prepared by tableting in a standard tablet press, either manual or automatic types.

Alternatively, the dried cells may be formed into granules by a known granulation procedure. For example, the cell concentration in the form of a liquid slurry produced by ultrafiltration is mixed with sucrose and cellulose, and kneaded to a doughy consistency. The cell dough is then extruded in the form of noodles or ribbons, which are broken up and formed into granules by a granulation apparatus. The granule size is not critical, but desirably is of a small size, such as below 20 mesh (U.S. Standard Screen). The granules are dried in an oven at a relatively low temperature, such as 37°–40° C. until most of the moisture has been removed. The final moisture content is not critical, and desirably may range from about 1 to 3% water by weight.

Orally-administrable pellets, which may comprise tablets or granules as described above, are provided with an enteric coating for the purpose of the present invention. The material used to provide the enteric coating should be selected so that it is resistant to dissolving in the swine stomach, while dissolving in the swine intestines. The differences in pH between the stomach and intestines can be used to control the dissolving of the enteric coating. While the pH conditions of the stomach and intestines of swine vary with diet and time of day, in general, the pH of a swine stomach and of the gastric fluid is below 5.0, such as 4.0 to 4.5. The pH of the small gut may range from about 5.5 in the upper small gut to about 5.9 to 6.1 in the middle and lower small gut. Similarly, the pH of the large bowel and colon may range from about 5.8 to 6.1. Preferably, therefore, the enteric coatings used in the present invention are substantially insoluble in water at a pH below 5.0, while being slowly soluble in water at a pH of 5.8 to 6.2. With this mechanism, the coatings are not exposed to the pH conditions of the mouth long enough to be dissolved and the coatings can remain sufficiently intact in the stomach to protect most of the vaccine from destruction by the gastric juice. During transit through the small bowel, the coatings on the granules are gradually dissolved, and are completely dissolved or disintegrated at least by the time the vaccine reaches the colon. The killed cells are therefore released in the swine intestines for immunizing action in the swine colon.

When the swine are being fed continuously, such as with feeder pigs, the pH of the food mass in the stomach may vary from about 4.0 near the stomach wall to 5.7 to 6.1 at the center of the food mass. The average residence time of the food in the stomach may range from 1 to 2 hours. Preferably, therefore the coatings on the vaccine granules should require at least one hour to dissolve in water at pH 6.0 and 37° C. (the standard temperature).

Any enteric coatings which meet the foregoing pH conditions can be utilized in practicing the present invention. One enteric coating material which can be used is cellulose acetate phthalate. As is well known in the art, cellulose acetate phthalate may be plasticized with diethyl or dibutyl phthalate so that the coating is more resistant to cracking. For application, the enteric coating material may be dissolved in a suitable volatile organic solvent, and the enteric coat may be built up in a series of applications to assure that the coating will be complete and relatively uniform. One known procedure of this kind is referred to as the "Open-Pan Ladle Coating Process." For example, 30 to 40 parts by weight of cellulose acetate phthalate together with 8 to 10 parts of diethyl phthalate may be dissolved in 250 to 300 parts by weight of acetone to form a coating solution. Suitable enteric coating resins may also be used, such as acrylic resins prepared for use as enteric coatings. One such product is sold under the trademark "Eudragit L" by Röhm Pharma Gmbh, Darmstadt, West Germany. The release pH of Eudragit L can be increased where desired by mixing it with Eudragit S. The manufacturer describes Eudragit L as soluble in intestinal juice from pH 6.0 and Eudragit S as soluble from ph 7.0. These enteric coating materials are supplied in granular form containing 10% moisture; specified as Eudragit L90 and Eduragit S90 to indicate the 90% active content. Eudragit L or mixtures of L and S are soluble in alcohols and acetone which may be used for applying the coating. The coating materials may be plasticized with various plasticizers, such as polyethylene glycol, dibutylphthalate, triacetin, or castor oil. Satisfactory coating results, however, can be obtained using the Eudragit material without plasticizer addition.

The Wurster Coating Process can also be used to apply the enteric coatings. This process is described in U.S. Pat. Nos. 3,241,520 and 3,253,944. It is carried out as a commercially available service by Coating Place, Inc., Verone, Wis.

Where the swine are being fed continuously, a preferred coating contains from 5 to 20 parts by weight of Eudragit S in admixture with from 95 to 80 parts of Eudragit L. For example, 15 parts S with 85 parts L increases the release pH so that at least 75% and up to 90% of the coated granules pass through the stomach with the protective coatings substantially undissolved. There is complete release in the intestines because of the longer residence time (8 to 24 hours).

The enteric-coated oral vaccine of the present invention is preferably in the form of granules which can be readily mixed with swine feed material for administration to the animals. For example, such granules may range from about −20 mesh to +100 mesh (U.S. Standard Screen). The granules are mixed with a finely-divided feed material such as a ground feed used for baby pigs after weaning. Any swine or pig feed material can be used, such as a basal ration containing ground corn, rolled oats, soybean meal, minerals, and vitamins. The coated granules may also be mixed with vitamin-mineral fortified premixes which are later combined with the other feed ingredients by the pig raisers. Such pre-mix may also contain high protein feed materials such as soybean meal.

While the enteric-coated vaccine pellets of the present invention and the oral method of immunization may be applied to adult swine, such as breeding sows, an important use is with growing pigs. For example, the method may be applied to feeder pigs as soon as they are receiving solid feed, either shortly before or following weaning. For example, the vaccine administration may be started at the age of about 3 to 8 weeks. The method may also be applied to older pigs during their growth period prior to marketing. The pigs raised under field conditions are highly subject to swine dysentery infection with consequent economic loss due to lowering of the rate of weight gain and the feed efficiency. By increasing the resistance of the pigs to swine dysentery infection, optimum rates of weight gain may be maintained.

In practicing the present invention, it is desirable to administer a plurality of doses of the enteric-coated oral vaccine, such as from 3 to 15 doses. Preferably, such dose should provide at least 3 milligrams of the killed cells of *T. hyodysenteriae* (dry basis) per animal; the doses being administered daily (once every 24 hours), such as by admixture of the enteric-coated granules with a feed material. This dosing may be continued for a period of at least 5 days, such as from 5 to 15 days. In a preferred embodiment, the oral doses contain at least 4 mg. of the killed cells (dry basis) per dose, such as doses in the range of 4 to 6 mg. Since 1 mg. of the cells (dry basis) contains about $2.5 \times 10^9$ cells, a dose of 5 mg. will provide approximately $1.2\times10^{10}$ cells. Therefore, in accordance with the present invention, massive quantities of the killed cells are delivered to the swine colon for immunizing action therein.

In applying tablet and granule coatings, a dye may be included as a colorant for the coating. This permits the coating to be more readily inspected for thickness and uniformity, and makes it easier to detect imperfections in the coatings. In practicing the present invention, it is desirable to use a dye in the enteric coatings of the present invention, although it is not essential with respect to the desired immunizing action. Suitable dyes include Lake Blue No. 2 and crystalline violet dye.

This invention is further illustrated by the following examples.

EXAMPLE I

Organism: The microorganism, *Treponema hyodysenteriae,* Strain 204 (ATCC No. 31287) was grown in Trypticase Soy Broth containing 5–10% sterile Fetal Calf Serum (GIBCO Laboratories, Grand Island, N.Y.) in test tubes, 500 cc Erlenmeyer flask, 4-liter glass jugs and in a 25-liter pilot New Brunswick fermentor. The growth culture was maintained until log phase growth ceased. The culture was inactivated by addition of formalin to 0.2% concentration. 50:50 $H_2$:$Co_2$ or no gas was used to maintain the gaseous atmosphere in the fermentor during the growth period. After the fermentation had been completed, the cells were concentrated in liquid mass by ultrafiltration.

The cell culture was forced by positive air pressure through a 100,000 molecular weight size membrane. The cell slurry was concentrated to a final concentration of 4.0 milligrams dry weight measurement per ml of culture. Ten percent (10%) by volume sterile milk stabilizer, (50% Non-fat dry milk powder in 50% $H_2O$) was added to the antigen *T. hyodysenteriae* slurry. E.g. 750 ml culture at 4 milligrams antigen/ml or 3.0 gram of antigen added to 75 ml milk stabilizer containing 37.5 grams dry powdered milk and 37.5 ml $H_2O$. The antigen milk stabilizer mixture was freeze-dried in a commercial freeze drier for 18 hours. The temperature was never allowed above 37° C. during the drying of the mixture. 66.20 grams of dried material was recovered from the drying process.

Capsule Preparation: Ten percent (10%) by weight dry soluble starch was added to the dried material giving the following components:

3.0 grams active antigen *T. hyodysenteriae* (killed cells-dry basis)

0.3 grams powdered milk stabilizer 0.33 grams soluble starch binder 0.5 Gram mixture (3 mg dry basis active *T. hyodysenteriae* antigen) of the above mixture was placed in a hand-operated pellet press. A ⅜" punch and die set was used to give a tablet of approximately ⅜" thickness by ½" in diameter.

Each tablet was coated with an enteric coating which upon contact in a chemical environment pH 6 or greater, will degrade and release the antigenic material into the colonic lumen. The coating is not soluble at the stomach pH.

Enteric Delivery System:

1. Enteric Coating Solution—(36.0 grams of cellulose acetate phthalate, 9.0 grams of diethyl phthalate, and 0.2 grams of crystalline violet dye) was diluted into 255 grams of reagent grade acetone. (For a description of a similar procedure, see C. J. Malm, J. Amer. Phar. Assoc, Science Edition, Vol. 40, p. 520, 1951.)
2. Enteric Coat Application—Each tablet was air blasted to remove dust and was submerged under the surface of the coating solution at least twenty times, with complete air drying of tablets between coatings.
3. Wax Coating—The enteric coating was further protected from $H_2O$ uptake by application of a white wax ("Be Square" 195, Petrolite Corporation, Bareco Division, Tulsa, Okla). This was liquified in the GI tract, and did not inhibit the antigen release in the colon. Ten (10) grams of "Be Square" 195 was beads were dissolved in 10 ml of acetone. Each enteric coated tablet was submerged at least twice in the liquid wax solution. The wax coat was allowed to dry prior to tablet bulking and storage. Stearic acid or other fatty acid or fatty acid triglyceride can also be used as an auxilliary coating to further protect the vaccine in the stomach. The fatty acids and triglycerides will be digested off the granules in the small gut.

Parenteral Vaccines:

The test also included administration of parenteral vaccine prepared as follows: The concentrated liquid slurry described above (4.0 mg. *T. hyodysenteriae* cells dry basis per ml) was diluted from 4.0 mg/ml to 1.0 mg/ml with a 20% solution of sterile aluminum hydroxide adjuvant. The resulting parenteral vaccine contained about $2.5\times10^9$ killed cells per milliliter.

Materials and Methods

Experimental Animals—Sixteen (16) pigs from a herd with no history of swine dysentery were placed in swine testing facilities at approximately five weeks of age and fed a 16% protein grown ration containing no drugs.

Preparation of Vaccines—An orally delivered enteric release vaccine and a parenteral vaccine containing *Treponema hyodysenteriae* Isolate B204 (ATCC No. 31287) with aluminum hydroxide as adjuvant was prepared.

Preparation of Inoculum—Cultures of *Treponema hyodysenteriae* (Isolate B204) were grown approximately 24 hours in aerobically prepared trypticase soy broth containing 10% fetal calf serum under deoxygenated $H_2$:$CO_2$ at 37° C. Seventy-five (75) ml of whole culture containing approximately $5\times10^8$ organisms per ml was administered to each pig via stomach tube following a 48 hour starvation period. The isolate of *T. hyodysenteriae* had not been passaged more than eight (8) times in vitro.

Experimental Design—The sixteen (16) pigs were randomly assigned to individual pens. The pigs were immunized as follows:

| Group | No. of Pigs | Parenteral Vaccine Subcutaneous* | Parenteral Vaccine Intraperitoneal* | Oral Vaccine* |
|---|---|---|---|---|
| I | 4 | − | + | + |
| II | 4 | + | − | + |
| III | 8 | − | − | − |

*+ = administered; − = not administered.

On day 0, the pigs in Group I were injected with 5ml/pig of the parenteral vaccine. Pigs in Group II were injected with a similar amount/pig by subcutaneous route. On day 14, a 5ml/pig booster vaccination was given by respective routes. On day 19, each pig in Groups I and II were given one (1) oral tablet per day through the 29th day. On day 30, all pigs were weighed. Feed was withheld on days 30 and 31. On day 32, rectal swabs were collected and all pigs were challenged with *T. hyodysenteriae* as described above. Clinical evaluation of response to challenge was recorded for each pig on a twice daily basis for 40 days post inoculation. On day 40 post-inoculation, each pig was weighed.

Evaluation of Response to Challenge—Each pig was observed twice daily and 3 clinical parameters were scored on a scale of 1 to 3. The results are shown in Table A.

TABLE A

| Clinical Response | Group | | |
|---|---|---|---|
| | I | II | III |
| | N=4[a] | N=4 | N=8 |
| Diarrhea: | | | |
| Day of Onset[b]/Post Inocul. | 16 | 5.2 | 13.6 |
| Days Duration | 4 | 8.2 | 11.8 |
| No. Affected | 4 | 4 | 6 |
| Dysentery: | | | |
| Day of Onset/Post Inocul. | 25.7 | 24.2 | 17.6 |
| Days Duration | 3.2 | 2.5 | 5 |
| No. Affected | 2 | 2 | 5 |

| General Condition: | 1 = Normal |
| | 2 = Gaunt, mildly inactive |
| | 3 = Emaciated, moribund |
| Feces Consistency: | 1 = Normal, firm |
| | 2 = Soft, not formed |
| | 3 = Liquid |
| Feces Composition: | 1 = Normal |
| | 2 = Increased mucus |
| | 3 = Large amount of blood present |

[a]N equals number of pigs per group
[b]Study terminated at 40 days. Calculations are based on a value of 40 assigned to each pig which remained normal.

Observation of *T. hyodysenteriae* Like Organisms—Rectal swabs were collected. A drop of each sample was reviewed under a dark field microscope observation. There was significant increase in the numbers of *T. hyodysenteriae* like organisms in clinically affected pigs which was considered evidence of an ongoing swine dysenteriae infection.

Weight Gain—The average weight gain during the period from day of challenge inoculation to the day of study termination was compared between vaccinated and non-vaccinated groups. The results are shown in Table B.

TABLE B

| | Group | | |
|---|---|---|---|
| | I | II | III |
| Days Post Test Initiation | IP-Oral | SC-Oral | Controls |
| 0 | 26.0 | 27.6 | 31.1 |
| 40 | 103.0 | 110.2 | 94.0 |
| Total Average Gain | 77.0 | 82.6 | 62.9 |
| per pig | | | |

EXAMPLE II

Enteric coated granules can be prepared by concentrating fermentor grown *Treponema hyodysenteriae* culture to about 64 mg dry weight/ml. Using such a concentrated antigen slurry it is combined with the other ingredients in the following proportions:

1500 cc antigen slurry
11.5 kilo sucrose
3.5 kilo microcrystalline cellulose
0.2% dry weight Lake blue No. 2 dye
$H_2O$ added as needed for obtaining proper texture Once this mixture is partially mixed the moistened mass of material is run through a commercial extruder at least three times to provide a uniform mix of antigen to carrier. The cylindrical pieces are then shaped into uniform beads in a manumerizer. The bead preparation is dried at least 1-8 hours leaving 1-3% moisture content. An enteric coating is then applied to the beads by either the Wurster or an open-pan, ladle type coating process, as previously identified. A preferred coating is a mixture of 85 parts by weight of Eudragit L 90 with 15 parts Eudragit S 90, using acetone or ethanol as the carrier solvent for applying the coating. (Eudragit L 90 and S 90 are sold by Röhm Pharma Gmbh, Darmstadt, West Germany.)

The enterically coated beads prepared as described will contain approximately 10% containing immunizing antigen (dry basis) can be administered in the following manner:

A. Remove all feed from swine (viz. weaned baby pigs) to be immunized 24 hours prior to treatment.
B. Mix the enteric coated granules with 10-20% of the daily required feed in a 1:1 ratio.
C. Each pig whould receive an average of 6-10 mg immunizing antigen/day, which determines the average amount of feed to be given to a group of pigs.
D. Feed untreated feed free choice during part of the day, but withhold feed overnite.
E. Repeat this feeding and withholding procedure for 5-10 days.

EXAMPLE III

Antigenic vitamin-mineral premixes can be prepared by mixing the immunizing granules prepared as described in Example II with standard pig feed fortification premixes. For example, the granules containing 10% of the *T. hyodysenteriae* cells (dry basis) are mixed with the following premix in the amount 100 grams granules per 7.5 pounds of a vitamin-mineral premix. The following premix is illustrative:

| Vitamin A | USP UNITS | 600,000 | per lb. of premix |
| Vitamin D3 | USP UNITS | 600,000 | " |
| Vitamin E | I Units | 200 | " |
| D-Calcium Pantothenic | mg. | 800 | " |
| Niacin | mg. | 1,600 | " |
| Niacin | mg | 4,000 | " |
| Chlorine Chloride | mg. | 20,000 | " |
| Vitamin B 12 | mg. | 2 | " |

-continued

| B.H.T. | mg. | 22,680 " |
| Manganese | mg. | 10,886 " |
| Zinc | mg. | 10,000 " |
| Iron | mg. | 3,628 " |
| Copper | mg. | 362 " |
| Iodine | mg. | 225 " |
| Cobalt | mg. | 36 " |
| L-Lysine | mg. | 2,500 " |
| Antigenic Graules (10%) | gr. | 13.3 " |

The above antigenic premix is then incorporated in pig feed in the amount of 7.5 pounds per ton. The following basal ration formula is illustrative:

```
1307   Corn (ground #2)
 200   Rolled Oats
 435   Soybean Meal (44% solvent)
  25   Di-Calcium Phosphate
  15   Feeding Lime
  10   Iodized Salt
+  7 ½ Antigenic Vitamin-Mineral Premix
2000 lbs.
```

The foregoing example and data illustrate the oral administration of enteric-coated tablets for increasing the resistance of swine to swine dysentery infection. The companion parenteral administration can be omitted and the oral administration used alone. However, the combination procedure is believed to enhance the effectiveness of the oral administration, as described in the co-pending application Ser. No. 935,062 of Delbert L. Harris and Robert A. Goodnow, filed on even date herewith, and entitled "Method of Increasing the Effectiveness of Oral Vaccination for Swine Dysentery."

I claim:

1. An oral preparation for increasing the resistance of swine to swine dysentery infection, comprising enteric-coated orally-administrable pellets containing concentrated killed cells of a virulent isolate of *Treponema hyodysenteriae,* said enteric coating being resistant to dissolving in the swine stomach while dissolving in the swine intestines to release said cells for immunizing action.

2. The preparation of claim 1 in which said killed cells of *Treponema hyodysenteriae* are prepared from isolate B204 (ATCC No. 31287).

3. An oral preparation for increasing the resistance of swine to swine dysentery infection, comprising enteric-coated orally-administrable pellets containing concentrated killed cells of a virulent isolate of *Treponema hyodysenteriae,* said enteric coating being substantially insoluble in water at a pH below 5.0 while being slowly soluble at a pH of 5.8 to 6.2, the coatings on said pellets requiring at least one hour to dissolve in water at 37° C. and pH 6.0.

4. The method of increasing the resistance of swine to swine dysentery infection, characterized by orally administering to swine while free of active swine dysentery infection a plurality of doses of enteric-coated pellets containing concentrated killed cells of a virulent isolate of *Treponema hyodysenteriae,* said enteric coating being resistant to dissolving in the swine stomach while dissolving in the swine intestines, and said doses providing at least 3 milligrams of said cells (dry basis) per animal per dose.

5. The method of claim 4 in which said killed cells of *Treponema hyodysenteriae* are prepared from isolate B204 (ATCC No. 31287).

6. The method of increasing the resistance of pigs to swine dysentery infection, said pigs being free of active swine dysentery infection but subject thereto, comprising preparing enteric-coated granules containing concentrated killed cells of a virulent isolate to *Treponema hyodysenteriae,* said enteric coating being resistant to dissolving in the swine stomach while dissolving in the swine intestines, mixing said granules with a finely-divided feed material for pigs, and feeding said mixture to the pigs at least once every 24 hours for a period of at least 5 days, each of said feedings providing at least 3 milligrams of said cells (dry basis) per animal.

7. The method of claim 6 in which said killed cells of *Treponema hyodysenteriae* are prepared from isolate B204 (ATCC No. 31287).

8. The method of claim 6 in which said enteric coating is substantially insoluble in water at a pH below 5.0 while being slowly soluble in water at a pH of 5.8 to 6.2, the coatings on said granules requiring at least one hour to dissolve in water at 37° C. and pH 6.0.

9. The method of claim 8 in which said killed cells of *Treponema hyodysenteriae* are prepared from isolate B204 (ATCC No. 31287).

10. An antigenic premix containing vitamins and minerals for administration to growing pigs characterized by also containing enteric-coated granules containing concentrated killed cells of a virulent isolate of *Treponema hyodysenteriae,* said enteric coating being resistant to dissolving in the swine stomach while dissolving in the swine intestines to release said cells for immunizing action.

11. The antigenic premix of claim 10 in which said killed cells of *Treponema hyodysenteriae* are prepared from isolate B204 (ATCC No. 31287).

12. The antigenic premix of claim 10 or claim 11 in which said enteric coating is substantially insoluble in water at a pH below 5.0 while being slowly soluble at a pH of 5.8 to 6.2, the coatings on said granules requiring at least one hour to dissolve in water at 37° C. and pH 6.0.

* * * * *

UNITED STATES PATENT OFFICE
CERTIFICATE OF CORRECTION

Patent No. 4,152,413          Dated May 1, 1979

Inventor(s) Robert A. Goodnow

It is certified that error appears in the above-identified patent and that said Letters Patent are hereby corrected as shown below:

Col. 5, line 29, change "31287" to --31212--.

Col. 6, line 54, change "31287" to --31212--.

Col. 9, line 48, change "31287" to --31212--.

Col. 10, line 15, change "31287" to --31212--.

Col. 10, line 30, change "31287" to --31212--.

Col. 10, line 38, change "31287" to --31212--.

Col. 10, line 49, change "31287" to --31212--.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks